United States Patent [19]

Morris et al.

[11] Patent Number: 4,795,262

[45] Date of Patent: Jan. 3, 1989

[54] LIQUID CHROMATOGRAPHY ABSORBANCE DETECTOR

[75] Inventors: Michael D. Morris, Ann Arbor, Mich.; Teng-Ke J. Pang, Palo Alto; Konan Peck, San Leandro, both of Calif.

[73] Assignee: The Regents of the Univerity of Michigan, Ann Arbor, Mich.

[21] Appl. No.: 79,026

[22] Filed: Jul. 29, 1987

[51] Int. Cl.⁴ ..................... G01N 21/01; G01N 21/85
[52] U.S. Cl. ..................................... 356/436; 356/410
[58] Field of Search ................. 356/72, 410, 411, 436, 356/129; 350/103

[56] References Cited

U.S. PATENT DOCUMENTS

| | | | |
|---|---|---|---|
| 3,628,872 | 12/1971 | Miranda . | |
| 4,126,396 | 11/1978 | Hartman et al. . | |
| 4,192,614 | 3/1980 | deMey, II et al. | 356/410 |
| 4,199,260 | 4/1980 | Kusnetz et al. | 356/411 |
| 4,202,600 | 5/1980 | Burke et al. | 350/103 |
| 4,432,649 | 2/1984 | Krause . | |
| 4,468,124 | 8/1984 | Berick et al. | 356/411 |
| 4,475,813 | 10/1984 | Munk | 356/410 X |

OTHER PUBLICATIONS

"The Amateur Scientist", *Scientific American,* published Apr. 1986, by Jearl Walker.

Pittsburgh Conference, presentation with slides, Mar. 1986, Michael D. Morris et al.

"Liquid Chromatography Absorbance Detector with Retroreflective Array for Aberration Compensation and Double Pass Operation", Nov. 1985, T. J. Pang and M. D. Morris.

*Primary Examiner*—Vincent P. McGraw
*Attorney, Agent, or Firm*—Harness, Dickey & Pierce

[57] ABSTRACT

This invention relates to an absorbance detector particularly adapted to liquid chromatography testing. In modern chromatography techniques, light is focused within a small capacity test sample cell, and an optical system is provided to measure the absorbance of various frequencies of light to thereby identify the existence of selected compounds. Inaccuracies of presently available detecting devices result since localized heating within the test cell generates localized index of refraction variations which refract the light in a random fashion such that it is not sensed by the detector. Additional distorting effects are caused by imperfections in the optical surfaces of the system and turbulence due to fluid flow within the sample cell. In accordance with this invention, an appropriate phase conjugator in the form of a retroreflective array is placed in the path of light exiting the sample cell. The array redirects the light rays along their original paths such that they are again distorted but in a reverse sense from the original distortion. In this manner, all of the distorting effects are compensated for. In addition, various means are employed to eliminate the effects of specular reflection from the various optical elements within the system.

20 Claims, 3 Drawing Sheets

LIQUID CHROMATOGRAPHY ABSORBANCE DETECTOR

BACKGROUND AND SUMMARY OF THE INVENTION

This invention relates to an improved liquid chromatography absorbance detector and particularly to one that provides cancellation of the effects of refractive index gradients and other distortion sources within a sample test cell.

Liquid chromatography is a common analytical procedure used primarily for the separation and detection of substances by differential, rates of migration as the substances are equilibrated between a stationary finely divided medium contained in a narrow column, a nonvolatile solvent which is pumped through the column. After the compounds have been separated by passage through the column, they must be detected and quantified. The detection/quantification process most commonly used is measurement of the absorption measurement of the molecules in the ulraviolet/visible region of the spectrum. In general, the detection process employs broad spectrum or monochromatic light which is passed through a test cell containing a liquid sample and the absorbance of selected frequencies of light is sensed by an absorbance detector and evaluated. The absorbance detector converts the incident radiation to a corresponding electrical signal which provides a measure of the absorption characteristics of the substance being characterized.

Although presently available liquid chromatography devices operate satisfactorily, there is a continuing need to improve their measurement accuracy by reducing noise which limits sensitivity. As light is transmitted through the test cell, a portion of the total energy of the light is absorbed which causes heating of the substances being evaluated. Such heating frequently causes localized refractive index variations which create tiny "lenses" which refract the light traversing the cell in a non-uniform manner. In certain liquid chromatographic techniques, the solvent mixture composition is continuously changed throughout the course of the separation in order to enhance the separation process. Since the solvent components do not usually have the same refractive indices, this process will make the optical system behave as a prism of continuously varying refractive power. If the solvent flow is not uniform, then there will be fluctuations in the refraction angle. In both cases, such randomly varying refraction causes random portions of the radiation passing through the test cell to escape detection, thereby increasing noise and decreasing measurement accuracy. The refraction effect caused by index variations is not constant with respect to time, and therefore, a static compensation approach cannot cancel distortions due to this effect. In addition to the above-mentioned phenomena, other factors such as imperfections in the optical elements of the system can cause portions of the radiation to be scattered so that each portion escapes detection.

In view of the foregoing, it is an object of this invention to provide an improved absorbance detector particularly useful for use with liquid chromatography devices. This detector compensates for the effects of distortions of the light as it passes through the test cell. In accordance with this invention, such improvements are achieved in part through the use of an approximate phase conjugator in the form of a retroreflective array.

The array causes rays passing through the test cell to be redirected closely along their same paths to again pass through the test cell. Such retracing causes the rays to be distorted in a reverse sense from the original distortion, thus "undoing" the original distortion and thereby compensating for it. Thereafter, radiation which has passed through the sample is separated from incident radiation by a beam splitter. Use of the retroreflective array enables distortion compensation to occur at a rate which is much faster than the relatively slow rate of the time dependent changes within the cell. This design further causes the light rays to pass through the sample twice, thereby doubling the signal obtained from the sample.

The use of retroreflective arrays in absorbance test apparatus, in general, is previously known as exemplified by U.S. Pat. No. 3,628,872 issued to Miranda. That patent sought to eliminate the effects of the non-planar optical surfaces of a test cell such as a cylindrical test tube and employed a retroreflective array for such compensation. The chromatography device in accordance with this invention, however, differs in many fundamental respects from that described in Miranda. Miranda teaches the use of a collimated light being passed through a large sample cell in the form of a conventional test tube. In modern liquid chromatographic practices, it is necessary to limit the volume of the sample cell, usually to one microliter or less. In accordance with the present invention, light is focused within a relatively small test cell. The Miranda patent does not comprehend that the efficiency of a retroreflective array is enhanced if the light strikes it nearly perpendicularly. In accordance with this invention, the light is collimated after passing through the sample and prior to exposure to the array. A retroreflective array is not optically perfect since a portion of the light striking its surface is simply reflected such that the angle of incidence equals the angle of reflection. Such specular reflection may arise from front surface reflections and from inteference effects between beams reflected from array elements. Specular reflection constitutes a source of noise since the reflected rays do not retrace their original paths. As a means of addressing this source of error, the present invention eliminates the effects of such direct reflection by slightly tipping the array with respect to the optical axis of the system such that reflected rays escape the optical path coupled to the detectors. The Miranda patent further does not comprehend means for eliminating the effects of light that is reflected directly from the planar surfaces of the test cell. As a means of eliminating such influences, optical mechanisms are provided to prevent the detectors from being influenced by such specular reflection.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
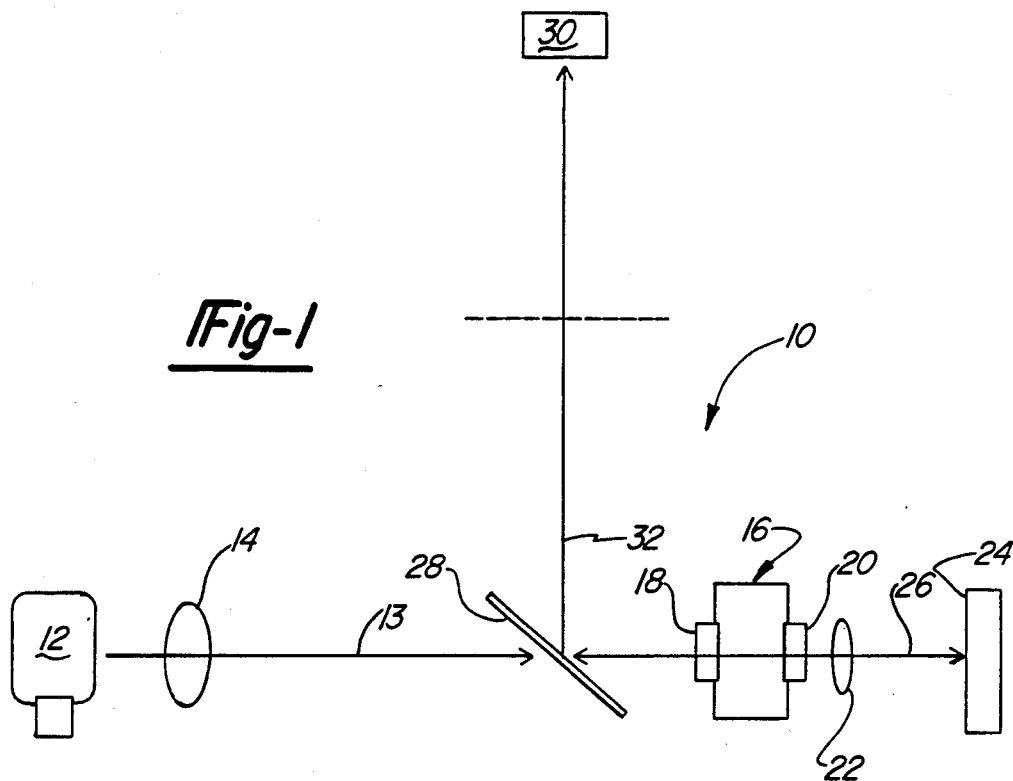
FIG. 1 is a diagrammatic view of a first embodiment of an absorbance detector in accordance with this invention.

FIG. 1 illustrates a chromatography absorbance detector in accordance with the first embodiment of this invention which is generally designated by reference number 10. Light source 12 which may be a monochromatic or broad spectrum type provides a source beam 13 for operation of the absorbance detector. Lens 14 is interposed in the light path from light source 12 and serves to focus source light 13 within test cell 16. Although lens 14 is illustrated diagrammatically as a single element refractor lens, multiple element or reflector systems may be used. Lens 14 is designed to cause rays from source 12 to be focused within test cell 16. Such focusing serves to minimize the volume requirements of test cell 16. Test cell 16 includes optical entrance window 18 and exit window 20. The material being characterized by absorbance detector 10 flows within test cell 16 from the chromatograpy column (not shown). The primary light beam 26 exiting window 20 passes through lens 22 which collimates these light rays such that they become nearly parallel. Retroreflective array 24 is imposed within the path of primary light beam 26. Light which is redirected from array 24 defines secondary light beam 32 which retraces the original path of primary light beam 26 and strikes beam splitter 28 of conventional construction, which directs secondary beam 32 toward detector 30. Detector 30 may be any desired type such as photoelectric single cell or array which detects incident radiation and provides an electrical signal output proportional to intensity.

Operation of absorbance detector 10 will now be described with reference to the above description and FIG. 1. As the primary light beam 26 passes through test cell 16, it may become distorted due to a number of factors. Since the source light is focused within test cell 16, localized heating of the substances being characterized may occur giving rise to localized index of refraction variations which change slowly over time. Similarly, turbulence effects caused by fluid flow within the test cell can produce similar distortions. Static errors such as imperfections in the optical surfaces of the system can also constitute a source of distortion. Therefore, the primary light beam 26 passing through test cell 16 can be said to be perturbed by a number of factors through the test cell. Such perturbations cause refraction of the light rays. Primary light beam 26 is collimated by lens 22 and strikes retroreflective array 24. Array 24 acts as a phase conjugator in that it directs incident light rays back along their original paths despite variations in incident angle. Since the perturbating factors within test cell 16 are static or occur slowly with respect to the speed of light, the reflected wave is passed through the perturbating medium in exactly the same way, and consequently, the distorting effects are automatically "undone" since the distortion of secondary light beam 32 is a reverse sense of the distortion of primary light beam 26. The wave passing back through test cell 16 is the complex conjugate of the original wave. This complex conjugated is separated from the primary beam through the use of beam splitter 28.

Various types of retroreflective material may be used to form array 24. These materials typically employ minute corner cubes having three mutually perpendicular reflecting surfaces.

These inventors have found that retroreflective array 24 may be comprised of Reflexite (Trademark of Reflexite Corporation) material which is intended for use on highway sign markers. However, superior performance would be achievable using a more optically perfect material which could be manufactured employing diffraction grating technology. The Reflexite material is not usable in the ultraviolet frequency ranges since the material is a second surface optical system which requires light to be transmitted through materials which absorb ultraviolet radiation. These inventors have also found that decreasing the element aperture dimensions of array 24 also improves the compensating effect provided by the array since across the smaller corner cubes the refractive index of the sample is more nearly constant and the effect of local inversion about the corner cube vertices does not distort the beam. In order to keep diffraction effects within acceptable limits, it is desirable to make the aperture dimension at least 50 times the wavelength of the incident light. This requirement must be balanced against the need for a small aperture dimension, as described. For light in the range of 0.2 to 0.4 micrometers wavelength, an array with 20 to 50 elements per millimeter would be acceptable.

Figure 2:
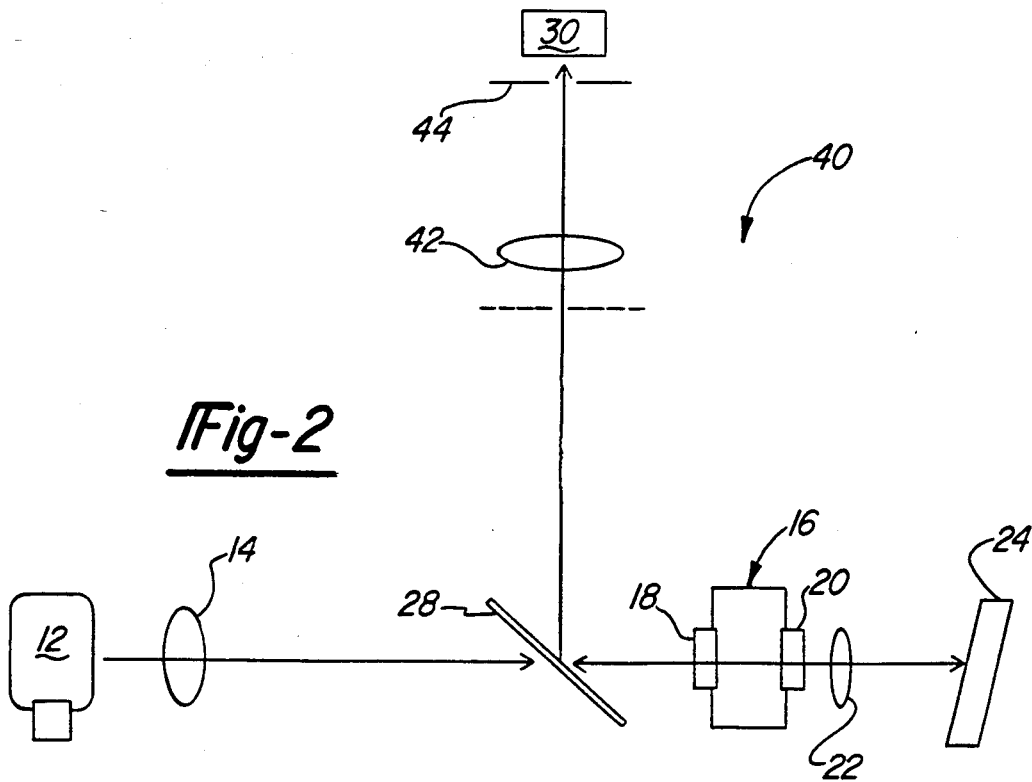
FIG. 2 is a diagrammatic view of an absorbance detector in accordance with a second embodiment of this invention.

FIG. 2 illustrates absorbance detector 40 in accordance with a second embodiment of this invention. For this embodiment, elements having configurations and functions equivalent to those described with reference to the first embodiment are identified by like reference numbers. Detector 40 differs in that lens 42 is added with aperture 44. These elements are provided to eliminate any specular reflection from the planar faces of entrance window 18 and/or exit window 20 of test cell 16. Such specular reflection is not sensed by detectors 30 since such rays do not focus in the plane of aperture 44. In addition, retroreflective array 24 is tilted slightly such that any light which is reflected through specular reflection is not retransmitted through the test cell and sensed by detector 30. It is desirable to eliminate such specular reflections since such rays do not retrace their original path and, therefore, would constitute an additional distorting factor.

Figure 3:
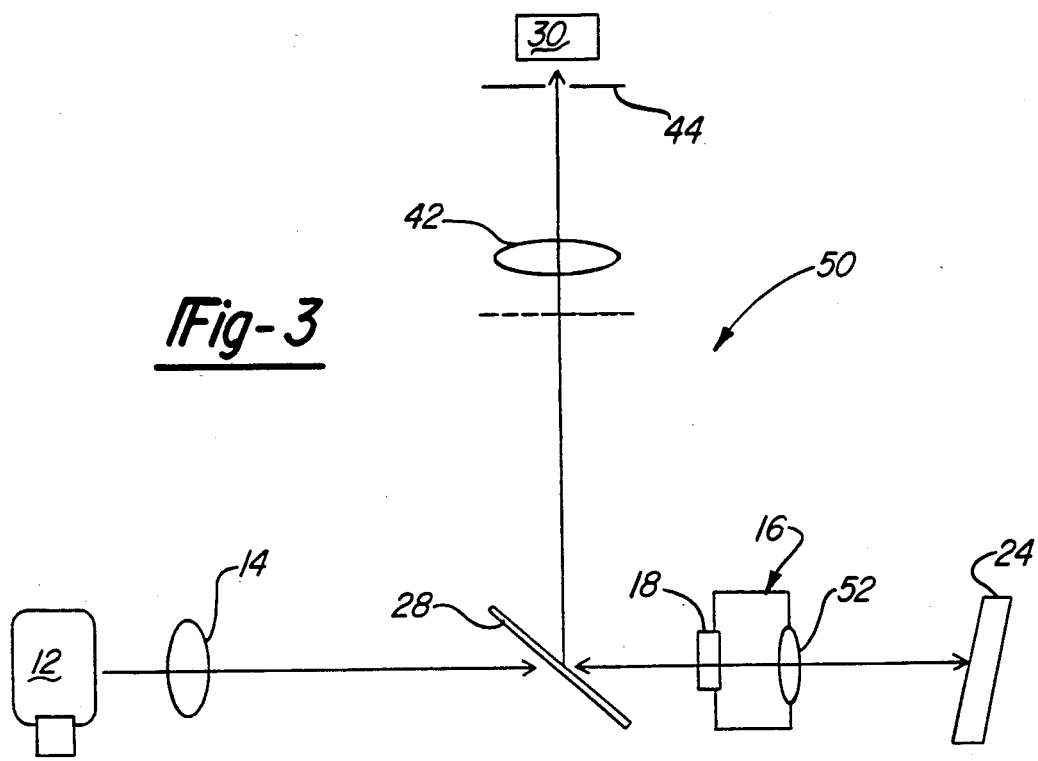
FIG. 3 is an absorbance detector in accordance with a third embodiment of this invention.

FIG. 3 illustrates absorbance detector 50 in accordance with a third embodiment of this invention, which embodiment is substantially identical to the second embodiment detector 40 except that lens 22 and exit window 20 are combined into a single element, referred to as exit lens/window 52. This embodiment otherwise operates precisely as absorbance detector 40 in accordance with the second embodiment of this invention.

Figure 4:
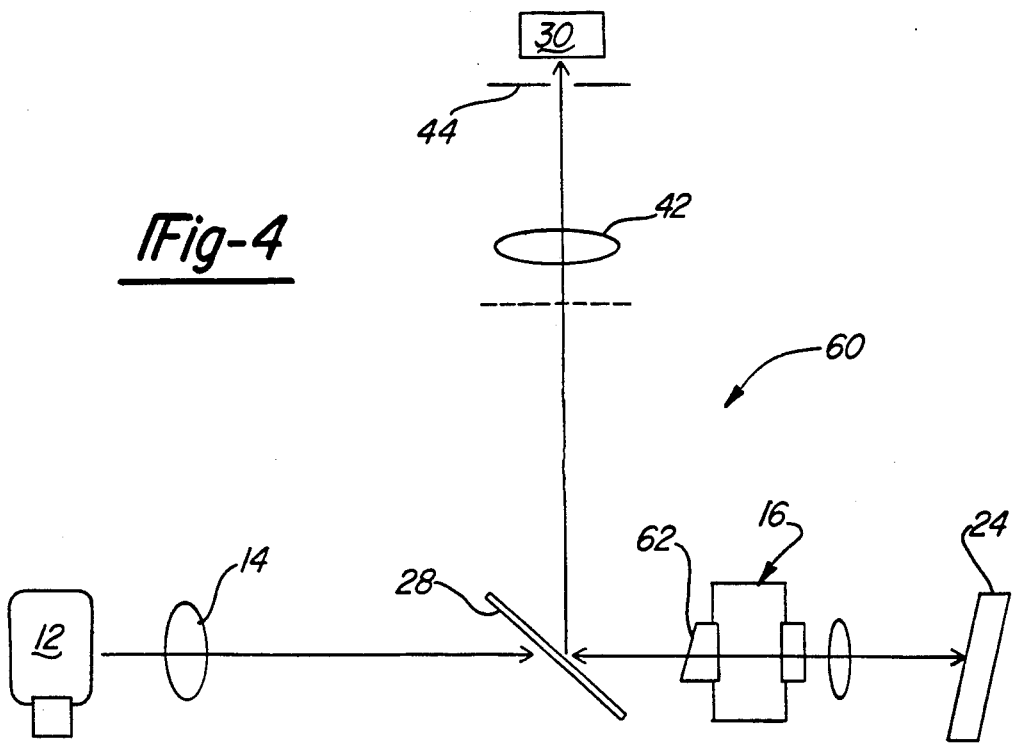
FIG. 4 is an absorbance detector in accordance with a fourth embodiment of this invention.

FIG. 4 illustrates absorbance detector 60 in accordance with a fourth embodiment of this invention. This embodiment varies from the second embodiment in that entrance window 62 includes a tilted front surface which directs specular reflection away from the path of detection by detector 30, and thus provides another means of eliminating the effects of such specular reflection.

Figure 5:
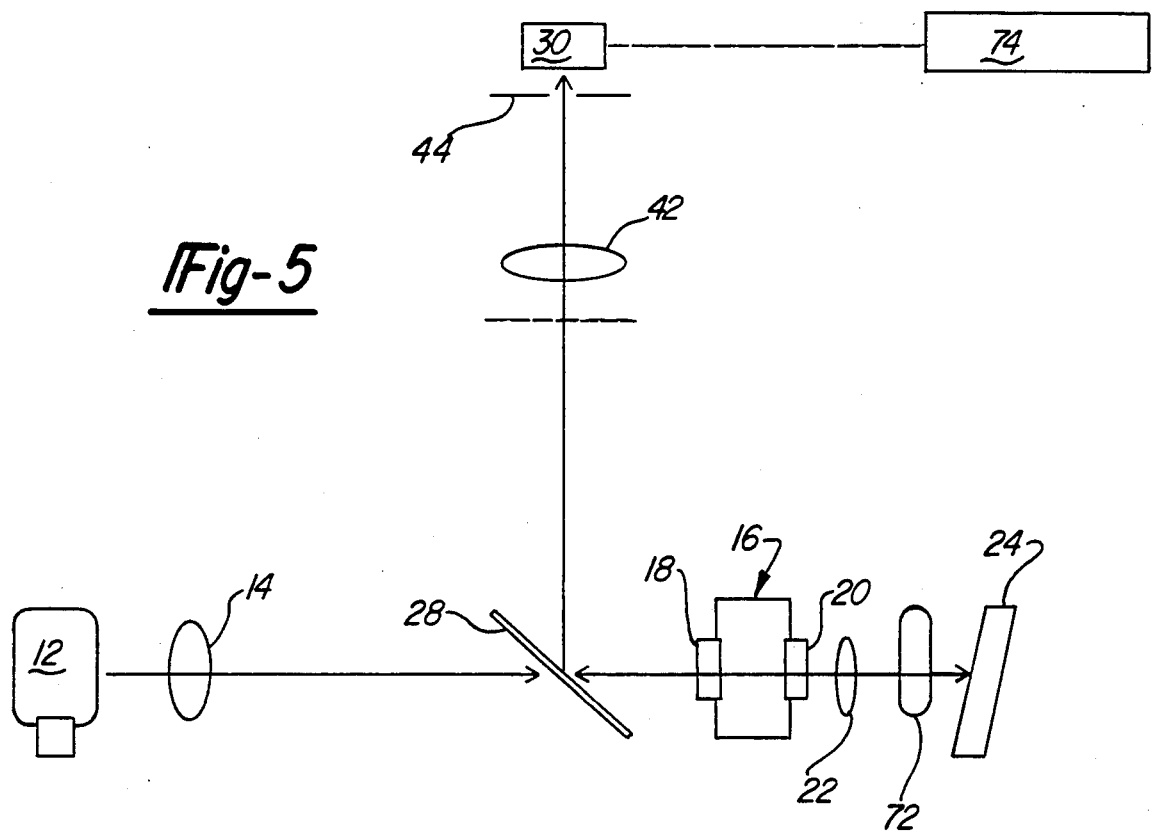
FIG. 5 is a diagrammatic view of an absorbance detector in accordance with a fifth embodiment of this invention.

FIG. 5 illustrates absorbance detector 70 in accordance with a fifth embodiment of this invention. This embodiment compensates for the distorting effect caused by fresnel reflection and other stray light sources within the system through the use of an optical chopper 72. Demodulator 74 is synchronized with chopper 72 to enable the system to distinguish between modulated light and other light which is detected.

While the above description constitutes the preferred embodiments of the present invention, it will be appreciated that the invention is susceptible to modification, variation, and change without departing from the proper scope and fair meaning of the accompanying claims.

What is claimed is:

1. An absorbance detector, comprising:
    a light source,
    a sample cell adapted to contain a substance to be characterized,
    first lens means for focusing source light from said light source in said sample cell while said source light becomes distorted within said sample cell and exits said sample cell defining a primary light beam,
    second lens means for collimating said primary light beam,
    a retroreflective array for redirecting said collimated primary light beam in a reverse direction defining a secondary light beam which travels along the path of said primary light beam such that said secondary light beam is distorted in a reverse sense from the distortion of said primary light beam such that said distortion is compensated for,
    a beam splitter for separating source light from said secondary light beam, and
    a detector for evaluating said secondary light beam.

2. An absorbance detector according to claim 1 wherein said retroreflective array is tipped from the optical axis of said primary light beam to prevent specular reflection from said retroreflective array from being detected by said detector.

3. An absorbance detector according to claim 1 further comprising third lens means and an aperture in the path of said secondary light beam to limit the transmission of specular reflection of elements within said detector.

4. An absorbance detector according to claim 1 wherein said sample cell includes a planar entrance window and an exit window.

5. An absorbance detector according to claim 4 wherein said planar entrance window is tipped from the optical axis of said source to prevent specular reflection from said entrance window from being detected by said detector.

6. An absorbance detector according to claim 4 wherein said exit window and said second lens means are integrated into a single element.

7. An absorbance detector according to claim 1, further comprising:
    an optical chopper which periodically interrupts said primary and secondary light beams and a demodulator coupled to said detector which is synchronized with said chopper such that said demodulator enables the effects of light which is not chopped to be eliminated.

8. An absorbance detector according to claim 1 wherein said retroreflective array is defined by a multiplicity of discrete optical elements and wherein said optical elements define an aperture at least fifty times the wavelength of said source light.

9. An absorbance detector according to claim 8 wherein said optical elements have a corner cube configuration.

10. An absorbance detector according to claim 1 wherein said retroreflective array is defined by a multiplicity of optical elements of a density of between 20 and 50 elments per millimeter.

11. An absorbance detector, comprising:
    a light source,
    a sample cell adapted to contain a substance to be characterized,
    first lens means for focusing source light from said light source in said sample cell while said source light becomes distorted within said sample cell and exits said sample cell defining a primary light beam,
    a retroreflective array for redirecting said primary light beam in a reverse direction defining a secondary light beam which travels along the path of said primary light beam such that said secondary light beam is distorted in a reverse sense from the distortion of said primary light beam such that said distortion is compensated for, said retroreflective array defined by a multiplicity is discrete optical elements having a density of between 20 and 50 elements per millimeter,
    a beam splitter for separating said source light from said secondary light beam, and
    a detector for evaluating said secondary light beam.

12. An absorbance detector according to claim 11 further comprising second lens means for collimating said primary light beam.

13. An absorbance detector according to claim 11 wherein said retroreflective array is tipped form the optical axis of said primary light beam to prevent specular reflection from said retroreflective array from being detected by said detector.

14. An absorbance detector according to claim 11 further comprising third lens means and an aperture in the path of said secondary light beam to limit the transmission of specular reflection of elements within said detector.

15. An absorbance detector according to claim 11 wherein said sample cell includes a planar entrance window and an exit window.

16. An absorbance detector according to claim 15 wherein said planar entrance window is tipped from the optical axis of said source to prevent specular reflection from said entrance window from being detected by said detector.

17. An absorbance detector according to claim 15 wherein said exit window and said second lens means are integrated into a single element.

18. An absorbance detector according to claim 11, further comprising an optical chopper which periodically interrupts said primary and secondary light beams and a demodulator coupled to said detector which is synchronized with said chopper such that said demodulator enables the effects of light which is not chopped to be eliminated.

19. An absorbance detector according to claim 11 wherein said retroreflective array is defined by a multiplicity of discrete optical elements and wherein said optical elements define an aperture at least fifty times the wavelength of said source light.

20. An absorbance detector according to claim 19 wherein said optical elements have a corner cube configuration.

* * * * *

UNITED STATES PATENT AND TRADEMARK OFFICE
CERTIFICATE OF CORRECTION

PATENT NO. : 4,795,262
DATED : January 3, 1989
INVENTOR(S) : Michael D. Morris et al It is certified that error appears in the above-identified patent and that said Letters Patent is hereby corrected as shown below:

On the title page under "Assignee", "univerity" should be --University--.

Column 1, Line 22 "ulraviolet" should be --ultraviolet--.

Column 2, Line 26 "chromatographic" should be --chromatography--.

Column 4, Line 1 "conjugated" should be --conjugate--.

Column 6, Line 7, "elments" should be --elements--.

Column 6, Line 23, "is" should be --of--.

Signed and Sealed this

Twenty-second Day of January, 1991

*Attest:*

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,795,262

DATED : January 3, 1989

INVENTOR(S) : Michael D. Morris, Teng-Ke J. Pang, Konan Peck

It is certified that error appears in the above-identified patent and that said Letters Patent is hereby corrected as shown below:

ON THE TITLE PAGE: After Item [54] please add the following paragraph:

--This invention was made with Government support under Grant Nos. MDN-021373 and RDS-022247 awarded by the National Science Foundation. The Government has certain rights in the invention.--

Signed and Sealed this

Twelfth Day of January, 1993

Attest:

DOUGLAS B. COMER

*Attesting Officer*     *Acting Commissioner of Patents and Trademarks*